(12) United States Patent
Henke-Sarmento

(10) Patent No.: US 8,473,027 B2
(45) Date of Patent: Jun. 25, 2013

(54) PROCESS FOR DRAPING BREAST MRI IMAGING COILS

(75) Inventor: Cynthia Ruth Henke-Sarmento, Lakewood, CO (US)

(73) Assignee: QSUM Biopsy Disposables LLC, Boulder, CO (US)

(*) Notice: Subject to any disclaimer, the term of this patent is extended or adjusted under 35 U.S.C. 154(b) by 992 days.

(21) Appl. No.: 12/372,925

(22) Filed: Feb. 18, 2009

(65) Prior Publication Data
US 2010/0004529 A1    Jan. 7, 2010

Related U.S. Application Data

(63) Continuation-in-part of application No. 12/217,351, filed on Jul. 3, 2008, now abandoned.

(51) Int. Cl.
*A61B 5/055* (2006.01)

(52) U.S. Cl.
USPC ........... 600/410; 600/415; 600/421; 600/422; 128/849; 128/853

(58) Field of Classification Search
USPC ............... 600/410–422; 324/307, 309, 318, 324/322; 128/849–854
See application file for complete search history.

(56) References Cited

U.S. PATENT DOCUMENTS

| | | | |
|---|---|---|---|
| D199,436 S | 10/1964 | Nall | |
| 3,310,459 A | 3/1967 | Guthrie | |
| 4,024,862 A | 5/1977 | Collins | |
| 4,041,942 A | 8/1977 | Dougan et al. | |
| 4,080,963 A | 3/1978 | Merry et al. | |
| 4,553,538 A | 11/1985 | Rafelson | |
| 4,666,432 A | 5/1987 | McNeish et al. | |
| 4,991,242 A | 2/1991 | Brown | |
| 5,095,910 A | 3/1992 | Powers | |
| 5,163,931 A | 11/1992 | Aldrett | |
| 5,363,845 A | 11/1994 | Chowdhury et al. | |
| 5,441,056 A | 8/1995 | Weber et al. | |
| 5,538,012 A | 7/1996 | Wiedner et al. | |
| 5,595,177 A | 1/1997 | Mena et al. | |
| 5,602,557 A | 2/1997 | Duerr | |
| 5,611,356 A | 3/1997 | Rothrum | |
| 5,699,802 A | 12/1997 | Duerr | |
| 5,732,712 A * | 3/1998 | Adair | 128/845 |
| 5,783,504 A | 7/1998 | Ehret et al. | |
| 5,860,420 A | 1/1999 | Wiedner et al. | |
| D410,084 S | 5/1999 | Tumey et al. | |
| 6,023,166 A | 2/2000 | Eydelman | |
| 6,105,578 A * | 8/2000 | Sommers et al. | 128/849 |
| 6,163,717 A | 12/2000 | Su | |
| 6,198,962 B1 | 3/2001 | Su | |
| 6,298,855 B1 | 10/2001 | Baird | |
| 6,306,132 B1 | 10/2001 | Moorman et al. | |

(Continued)

*Primary Examiner* — Ruth S Smith
(74) *Attorney, Agent, or Firm* — Marsh Fischmann & Breyfogle LLP

(57) ABSTRACT

A draping provides at least partial and preferably complete coverage of MRI coils, an MRI table and an MRI support system thereby protecting a patient and the equipment. Draping notch fold down flaps may be pushed into shaped apertures of an MRI apparatus by the patient's breast due to the design of the draping. This offers a barrier between the patient and the equipment pad providing the patient with warmth, comfort and protection from infectious diseases such as Methicillin-resistant staphylococcus aureus (MRSA). The draping reduces the clean up and improves the procedure turnaround time for the technologist.

19 Claims, 9 Drawing Sheets

U.S. PATENT DOCUMENTS

| | | |
|---|---|---|
| 6,493,572 B1 | 12/2002 | Su |
| 6,675,037 B1 | 1/2004 | Tsekos |
| 6,694,981 B2 | 2/2004 | Gingles et al. |
| 6,697,664 B2 * | 2/2004 | Kienzle, III et al. .......... 600/427 |
| 6,843,252 B2 | 1/2005 | Harrison et al. |
| 7,082,631 B2 | 8/2006 | Czop |
| 7,084,630 B2 | 8/2006 | Ludwig |
| 7,086,404 B2 | 8/2006 | Dusenbery et al. |
| 7,497,819 B2 | 3/2009 | White et al. |
| 7,717,117 B2 * | 5/2010 | Duarte .......................... 128/849 |
| 7,826,883 B2 * | 11/2010 | Hibner et al. ................. 600/407 |
| 8,079,365 B2 * | 12/2011 | Block et al. ................... 128/853 |
| 8,123,681 B2 | 2/2012 | Schaeffer |
| 2004/0249268 A1 | 12/2004 | Da Silva |
| 2005/0205099 A1 | 9/2005 | Gellerstedt et al. |
| 2005/0284487 A1 | 12/2005 | Gellerstedt et al. |
| 2006/0089600 A1 | 4/2006 | Bierman et al. |
| 2006/0094923 A1 | 5/2006 | Mate |
| 2006/0169290 A1 | 8/2006 | Harris et al. |
| 2006/0191540 A1 * | 8/2006 | Lamprich et al. ............. 128/849 |
| 2006/0270930 A1 | 11/2006 | Brasile |
| 2007/0142694 A1 | 6/2007 | Cutrer et al. |
| 2008/0065022 A1 | 3/2008 | Kyvik et al. |
| 2008/0214930 A1 | 9/2008 | Brasile |
| 2008/0243082 A1 | 10/2008 | Goodman |
| 2008/0275333 A1 | 11/2008 | Fain et al. |
| 2008/0294141 A1 | 11/2008 | Chen |
| 2009/0076457 A2 | 3/2009 | Bierman et al. |
| 2009/0149814 A1 | 6/2009 | Bailey et al. |
| 2009/0156882 A1 | 6/2009 | Chi Sing et al. |
| 2009/0188098 A1 | 7/2009 | Acosta et al. |
| 2011/0030702 A1 | 2/2011 | Czajka, Jr. et al. |

* cited by examiner

US 8,473,027 B2

PROCESS FOR DRAPING BREAST MRI IMAGING COILS

RELATED APPLICATIONS

This application claims priority as a continuation-in-part application of U.S. patent application Ser. No. 12/217,351, filed on Jul. 3, 2008, now abandoned, which is incorporated herein by reference in its entirety.

FIELD OF THE INVENTION

This invention relates generally to the field of Magnetic Resonance Imaging (MRI) and more specifically to a process and apparatus for draping breast MRI imaging coils.

BACKGROUND OF THE INVENTION

Nuclear Magnetic Resonance (NMR) was first developed in 1946 when two separate professors made the first successful nuclear magnetic resonance experiment to study chemical compounds. They were awarded the Nobel Prize of Physics in 1952. NMR is based on a physics phenomenon discovered in the 1930's, called nuclear magnetic resonance in which magnetic fields and radio waves cause atoms to give off tiny radio signals.

Paul Lauterbur, a professor of chemistry at the State University of New York, moved NMR from science to imaging by developing the second dimension of spatial orientation from the single dimension of NMR spectroscopy. The imaging industry labeled the technology Magnetic Resonance Imaging (MRI) in the mid 1980's. Peter Mansfield of Nottingham, England further developed this concept by utilizing gradients in the mathematics field. He showed how the signals may be mathematically analyzed providing a way to conduct a consistent technique. In 1970, Raymond Damadian discovered the basis for using MRI as a tool for medical diagnosis. He found that different kinds of animal tissue emitted response signals that lasted longer than non-cancerous tissue. Two years later he filed for a patent for an "Apparatus and Method for Detecting Cancer in Tissue". The patent was granted in 1974 and was the world's first patent issued in the field of MRI. In 1977 Dr. Damadian had constructed the first whole body MRI scanner. In 1983 the first "human" MRI scanner was installed in Europe and in 2002 approximately 22,000 MRI systems were in use worldwide performing over 60 million MRI examinations.

Since water constitutes about two thirds of the human body, hydrogen proton imaging with MRI is a logical use of the technology. The differences in water content among tissues and organs are easily differentiated by MRI. When the body is exposed to a strong magnetic field, the nuclei of the hydrogen atoms are directed into "order". When submitted to pulses of radio waves, the energy content of the nuclei changes. After an RF pulse, a resonance wave is emitted as the nuclei return to their previous state. The small differences in the oscillations of the nuclei are detected. This results in a very detailed image of tissues and organs in the investigated area of the body.

As MRI imaging technology steadily improved and techniques such as fat suppression were developed, breast imaging became feasible. In the early 1990's physicians began experimenting with breast imaging to see if breast cancer could be detected. MRI has proven to be a very useful modality for imaging the "dense" breast that regular x-ray has difficulty penetrating thus missing cancers hidden by dense tissue.

In the mid 1990s, a dedicated breast coil was developed that allowed the breast to be suspended with a patient in the prone position. In 2007 a very large study in the Lancet 2007; 370:485-92 "MRI for diagnosis of pure ductal carcinoma in situ (DCIS): a prospective observational study" determined that out of 7319 women who received MRI in addition to mammography over a 5 year period, breast MRI detected high grade DCIS 100% of the time compared to a 48% detection rate for mammography.

Due to the increase in breast MRI procedures and biopsies, a need for comfort and cleanliness has been noted by both the patients and MRI technologists. A primary concern has been to provide a protective covering of the MRI equipment, including the breast coil. In this regard, technologists have utilized sheets and pillowcases in an attempt to cover the equipment. However, the breast coil design makes it difficult to adequately protect the equipment and patient from fluids. For example, the use of sheets fails to protect the equipment padding which may be porous and retains body dirt, sweat, and bodily fluids. Cleaning is also an issue.

SUMMARY OF THE INVENTION

It has been recognized that the devices (e.g. sheets and pillowcases) currently used for covering MRI equipment are inadequate for a number of reasons. For instance, after folding a sheet or pillowcase in an attempt to cover the coils of an MRI apparatus for the patients and employees, the sheet or pillowcase often does not stay in the same place if the patient or technologist repositions a breast. Additionally, there is no patient protection available for inside and over the outside of the breast MRI coils if the manufacturer's coil padding is removed for breast access (e.g. for small-breasted women). In this regard, the present inventor has recognized that a draping may be necessary as the patient may have open wounds, skin diseases, etc. that may be passed to the next patient if complete sterilization of the padding or the equipment does not occur. A complete sterilization process often does not occur because it is a costly and time-consuming process.

Accordingly, the primary object of the invention is to provide a draping for MRI apparatuses that incorporate breast coils to protect the patient and equipment from any bodily contaminants such as sweat, dirt, bodily fluids or infectious disease.

Another object of the present invention is to reduce contact between a patient and an MRI apparatus.

A further object of the invention is to increase patient comfort when the patient is using an MRI apparatus.

Another object of the invention is to reduce the quantity of cleanup and improve an MRI procedure turnaround for MRI technologists.

In addressing one or more of the above objectives and in accordance with one embodiment of the invention, there is disclosed a draping for a Magnetic Resonance Imaging (MRI) apparatus. The MRI apparatus used with the draping may include at least one breast coil for imaging of a patient's breast and typically two breast coils for imaging two patient breasts. The draping broadly includes a barrier and an opening for receiving a patient's breast that extends through a portion of the barrier.

In one aspect, the barrier may be positionable to locate the opening over an aperture in the MRI apparatus, the aperture housing or otherwise containing a breast coil. Such aperture may be of any appropriate shape such as round, rectangular, or other shapes and configurations. The aperture may extend through a patient interface surface and into a housing of the MRI apparatus. The barrier may also be extendable away from the opening and may be positionable over a portion of the MRI apparatus such as a patient interface surface. In this regard, the barrier may be positionable between at least a portion of the patient interface surface and a portion of a patient. The barrier may be constructed of at least one pliable and/or absorbent material, and may be disposable and/or reusable.

In another aspect, a periphery of the barrier may be sized to encompass a periphery of the patient interface surface of the MRI apparatus. Moreover, a periphery or other portion of the barrier may include a securing member such as elastic, string or hook and loop that may allow the barrier to secure around and conform to the general shape of the MRI apparatus after the periphery of the barrier has encompassed the periphery of the patient interface surface. In one embodiment, at least a portion of the periphery of the patient interface surface may be defined by at least one ledge or other protruding device that may allow the draping to be removably attached to the MRI apparatus. As such and as will be described in more detail below, a single draping may be advantageously utilized in conjunction with a plurality of MRI apparatuses, each of the MRI apparatuses having housings, patient interface surfaces, apertures and/or the like of various sizes and dimensions.

In another aspect, the opening may have a periphery that may be sized to be encompassed by a periphery of the aperture. As such, the opening may be sized such that the opening is at least substantially aligned over or encompassed by the aperture of the MRI apparatus and thus primed for entry of a patient's breast when the barrier is positioned over the patient interface surface. In one embodiment, the opening may be at least partially defined by at least notch; in another embodiment, the opening may alternatively or additionally be defined by at least one hole.

In one variation, the opening may include a hole and a notch and the notch may extend away from the hole. Another variation contemplates that the opening may be at least partially defined by a plurality of notches each of which may intersect each other and/or emanate from a hole. Such arrangements may facilitate introduction of the patient's breast through the barrier and ultimately into the aperture in the MRI apparatus. More specifically, the use of a plurality of notches effectively increases the adjustability of the opening to accommodate breasts of various sizes while providing additional and varying degrees of protection and comfort for a patient. The hole may be circular, rectangular or even other shapes and of various dimensions to accommodate various types of MRI apparatuses and various sizes of breasts. Other embodiments contemplate that the draping may further include a second opening for accepting or receiving a breast. During positioning of the barrier over the MRI apparatus, the openings may be positioned over the apertures in the MRI apparatus and a technician may direct a patient to insert or position his or her breasts through the openings and the MRI apparatus apertures for an imaging procedure.

A further aspect contemplates that the draping may include at least a first flap and a second flap each being disposed adjacent the opening. In this regard, the flaps and the barrier may form an integral or otherwise continuous surface or draping extending from a breast coil or aperture to the patient interface surface of the MRI apparatus. The first and second flaps may be positionable between at least a portion of the MRI apparatus (e.g. breast coil) and a portion of a patient's breast that is positioned through the opening and within the aperture of the MRI apparatus. For instance, the aperture in the MRI apparatus may be surrounded by a sidewall such that the first and second flaps may be positionable between the sidewall and the portion of the patient's breast positioned through the opening and within the aperture. As such, the flaps and the barrier may advantageously reduce or otherwise prevent the transfer of germs, bacteria, viruses and the like between a patient undergoing an MRI procedure and various portions of the MRI apparatus. The flaps may be positioned into the MRI apparatus apertures prior to and/or during introduction of the patient's breast through the opening and into the aperture.

In one variation, each flap may be at least partially defined by adjacent pairs of notches of a plurality of notches, whereby each notch may emanate from a hole of the opening. For instance, a first notch and a second notch of the plurality of notches may partially define the first flap, and the second notch and a third notch of the plurality of notches may partially define the second flap. Moreover, the draping may include at least a third flap and a fourth flap each being disposed adjacent the opening. The third notch and a fourth notch of the plurality of notches may partially define the third flap, and the fourth notch and the first notch may partially define the fourth flap. Each flap may also be at least partially defined by more than adjacent pairs of notches. Additional flaps and notches may be included with the draping to provide additional degrees of patient protection, comfort, and the like. In one particular arrangement, the opening may include a rectangular hole, and a notch may emanate from each corner of the rectangular hole such that a flap may be adjacent each side of the rectangular hole. In another arrangement, the first flap may be generally opposed to the second flap. As such, protection of a patient's breast during an MRI procedure may be provided because both sides of the breast may be covered or shielded by the first and second flaps.

In an even further aspect, the draping may be usable on a plurality of different MRI apparatuses, each of the different MRI apparatuses including a patient interface surface and an aperture extending through the patient interface surface. The barrier may be positionable both to locate the opening over the aperture of each of the different MRI apparatuses, and between at least a portion of the patient interface surface of each of the different MRI apparatuses and a portion of the patient.

For instance, a periphery of the opening may be sized to be encompassed by a periphery of the aperture of each of the different MRI apparatuses. In another variation, the periphery of the barrier may be sized to encompass a periphery of the patient interface surface of each of the different MRI apparatuses. In this regard, a single draping may advantageously be used in conjunction with a number of MRI apparatuses regardless of the size, diameter, etc. of the patient interface surface or aperture of the MRI apparatuses. Some variations also contemplate that at least one securing member may be positionable to removably secure the barrier to a periphery of the patient interface surface of each of the different MRI apparatuses. Moreover, at least a portion of the periphery of the patient interface surface of each of the different MRI apparatuses may be defined by at least one ledge, and such ledge may accept or otherwise interact with the securing member to aid in removable securing the barrier to the MRI apparatus.

Some embodiments of the present invention provide various methodologies for using a draping with an MRI apparatus and/or constructing such a draping for instance. In one characterization, a method for reducing contact between a portion of a patient (e.g. breast) and a portion of a Magnetic Resonance Imaging (MRI) apparatus is provided, the MRI apparatus including a patient interface surface and an aperture extending through the patient interface surface. In some arrangements, the MRI apparatus may include a coil associated with or located within the aperture. Moreover, the MRI apparatus may have one or more pads, cushions, sleeves and/or strips of any appropriate shape, size and materials associated therewith that is or are situated or positionable within the aperture and/or on top of the patient interface surface. In some embodiments, the pads, cushions, etc. may be constructed of a flexible material.

Broadly, the method includes positioning a barrier over at least a portion of the patient interface surface, the barrier comprising at least one opening, and locating the opening over the aperture of the MRI apparatus. According to one aspect, the positioning step may include positioning the barrier over at least a portion of one or more of the aforementioned pads, cushions, sleeves and/or strips associated with the MRI apparatus. As such, a barrier or sheath may be created to prevent or otherwise reduce cross-contamination between a patient and portions of the patient interface surface, the pads, cushions, sleeves or strips, and/or other surfaces of the MRI apparatus and the barrier may also function as a cushion for a patient.

According to another aspect, the positioning step may further include arranging a periphery of the barrier to encompass a periphery of the MRI apparatus, or even a periphery of the patient interface surface. In one variation or as an additional aspect, the barrier may be removably secured to the MRI apparatus. For instance, the barrier may be secured to the patient interface surface of the MRI apparatus, and additionally, may be removable secured to a ledge associated with the patient interface surface. Further, the securing step may include manipulating at least one securing member interconnected to the barrier to detachably connect the barrier to the patient interface surface to restrict relative movement between the barrier and the MRI apparatus. Such at least one securing member may include at least one of a group including elastic, hook and loop, string, tape, snaps, ribbons, sticky glue, buttons, ties and tab hooks.

According to a further aspect, the locating step may further include aligning the barrier opening and the aperture of the MRI apparatus. Such an alignment step facilitates subsequent disposition or insertion of a breast through the barrier opening and into the aperture of the MRI apparatus. In one variation, such aspect may include arranging a periphery of the opening to be encompassed by a periphery of the aperture and in another variation, such aspect may include arranging a center axis of each of the opening and the aperture of the MRI apparatus to be collinear with each other.

In accordance with yet another aspect, the barrier may include at least one flap which may be adjacent the opening and may be positionable through the aperture of the MRI apparatus. For example, the barrier may have at least two flaps that are equidistantly spaced around the center axis of the barrier opening. Such additional flaps advantageously increase the relative degree of protection or reduction of cross-contamination in addition to patient comfort.

As another example, the locating step may further comprise disposing at least one flap to be within a portion of the aperture of the MRI apparatus and adjacent the coil. Disposition of at least one flap in such a location may further reduce or otherwise prevent cross-contamination (e.g. germs, disease) between a portion of the coil or other portion of the aperture and another object or a portion of the patient.

In one variation, the disposing step further may comprise advancing the flap into the portion of the aperture of the MRI apparatus. Such advancing step may include locating a patient breast through the barrier opening and aperture of the MRI apparatus, wherein the at least one flap may be interposed between at least a portion of the coil and at least a portion of the patient breast. The patient may be directed to locate the patient breast through the barrier opening. Such advancing step may also include pushing the flap into the portion of the aperture of the MRI apparatus, and the pushing may comprise at least one of a group comprising: folding, creasing, bending and flexing the flap. For instance, after the barrier opening is located over the aperture of the MRI apparatus, a hospital technician or other employee may fold or push the flap into the MRI apparatus aperture, and then the patient's breast may be disposed within the opening and the aperture.

In another variation, the disposing step may comprise maneuvering the flap at least partially away from the barrier opening, and arranging the flap to be within the portion of the aperture of the MRI apparatus. As such, the flap may essentially be pre-positioned in a protruding orientation from the barrier opening before the flap is placed into the MRI apparatus aperture. The maneuvering step may include at least one of a group comprising folding, creasing, bending and flexing. Moreover, the arranging step may comprise placing the flap into the portion of the aperture of the MRI apparatus, and in some approaches, the placing step may comprise at least one of a group comprising pushing and inserting the flap. For instance, after the flap has been maneuvered, the flap may be pushed, inserted or otherwise placed into the MRI apparatus aperture by a hospital technician, the patient, a machine, etc.

In even another variation after the disposing step, the method may include removing the barrier from the patient interface surface, and discarding the barrier. In some approaches, the patient's breast may be imaged using the MRI apparatus before the barrier is removed from the patient interface surface. Removing the barrier may further inhibits cross-contamination between the barrier and other surfaces such as the MRI apparatus and/or the patient.

In even another aspect, the method may include before the positioning step removing at least one member associated with a portion of the patient interface surface. Removing such a member facilitates the imaging of small-breasted patients. In one approach, the member being removed comprises a layer of flexible material, and such layer may be one of a group of padding and cushioning. In another approach, the member being removed may be adjacent the aperture of the MRI apparatus.

In another aspect, a method for reducing contact between a patient and a portion of a plurality of MRI apparatuses is provided, each of the MRI apparatuses including a patient interface surface and an aperture extending through the patient interface surface. In one arrangement, a plurality of the patient interface surfaces may be of a different size and a plurality of the apertures may be of a different size. The method broadly includes positioning a barrier over at least a portion of the patient interface surface of one of the MRI apparatuses without regard to the size of the patient interface surface, the barrier comprising at least one opening, and locating the opening over the aperture of the one of the MRI apparatuses without regard to the size of the aperture.

In one variation, the positioning step may further comprise arranging a periphery of the barrier to encompass a periphery of the patient interface surface of the one of the MRI apparatuses. In another variation, the locating step may further comprise arranging a periphery of the opening to be encompassed by a periphery of the aperture of the one of the MRI apparatuses. Other variations envision that the locating step may further comprise arranging a periphery of the opening to be encompassed by a periphery of the aperture of the one of the MRI apparatuses, and/or the method may further include, securing the barrier to the one of the MRI apparatuses.

In another aspect, a method may be provided for forming or manufacturing a draping that may be provided for reducing contact between a patient breast and a portion of a Magnetic Resonance Imaging (MRI) apparatus (e.g. patient interface surface, breast coil). It will be appreciated that other methods of forming a draping are contemplated. The method may include forming a pliable barrier of one or more layers. The one or more layers may be absorbent and may reduce leakage or the transfer of fluids, germs and disease from one side of the barrier to the other side of the barrier. Additionally, a securing member in the form of elastic, hook and loop, and the like may be appropriately secured about a periphery or other portion of the barrier to secure the barrier to a device, such as an MRI apparatus.

Either before or after the securing member is secured to the barrier, one or more padding members may be bonded, laminated or otherwise connected to one or more sides of the barrier. The padding member may be constructed of one or more types of materials such as felt, cotton, gelatinous materials and the like, and may be absorbent or non-absorbent. The method may further include appropriately forming or creating an opening through the barrier and the one or more padding members. In one embodiment, the opening may be formed by appropriately forming or creating one or more slits, slots or notches, and such slits, slots or notches may partially define at least one flap that may be positionable within an aperture of an MRI apparatus. In other embodiments, the opening may be formed by additionally or alternatively forming or creating a hole of any appropriately shape (e.g. circular, rectangular) that may also partially define at least one flap positionable within the aperture of the MRI apparatus.

It will be appreciated that the various steps, aspects and variations of the embodiments of the drapings and the methods disclosed herein may be utilized by other embodiments of the drapings and methods. Other objects and advantages of the present invention will become apparent from the following descriptions, taken in connection with the accompanying drawings, wherein, by way of illustration and example, an embodiment of the present invention is disclosed.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION

Figure 1:
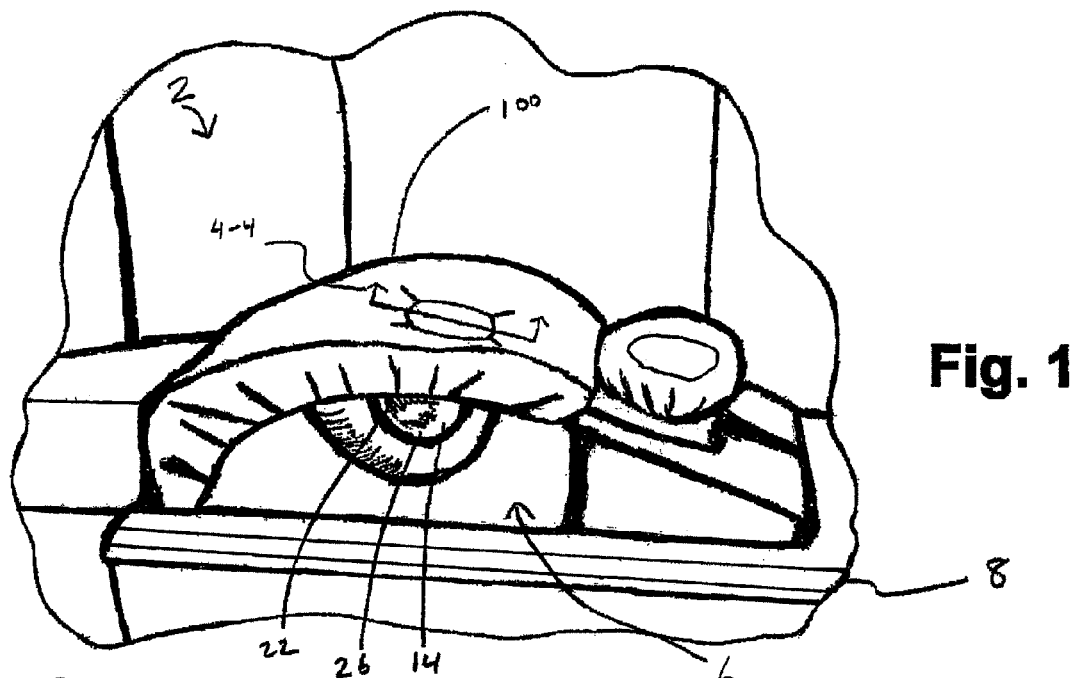
FIG. 1 illustrates a perspective view of an MRI apparatus including at least one aperture having a coil therein for the imaging of a breast of a patient, and including a draping positioned over the MRI apparatus.

FIG. 1 illustrates a Magnetic Resonance Imaging (MRI) apparatus 2 that may be used as part of an MRI system for imaging the breast of a patient. The MRI apparatus 2 may include a housing 6 appropriately disposed on a table 8, the table 8 adapted to be translatable into and out of the bore of a primary magnet as will be later described. An upper portion of the housing 6 may have a patient interface surface (not shown) that may be adapted to support the body of the patient. A portion of the patient interface surface and/or other portion of the housing 6 may include at least one ledge, hook or the like at any appropriate location or locations for securing a device to the MRI apparatus. For instance, a periphery of the patient interface surface may include a ledge or other protruding structure extending therefrom for removably attaching to a draping as will be described below.

A pair of shaped apertures 14 (only one being shown) may extend through the patient interface surface of the housing 6, each aperture 14 for pendulantly receiving a patient's breast during MR imaging of the breasts. Each aperture 14 has a coil (e.g. breast coil, not shown) associated therewith that produces RF signals that the MRI system uses to generate an image of the respective breast of the patient. Further, each aperture 14 may have a periphery 18 (illustrated in FIG. 4) and a sidewall 22 extending downward from the periphery 18 to a location within the housing 6. The apertures 14 may be circular, rectangular, and/or of other shapes and/or sizes.

Each coil may be associated with or otherwise appropriately mounted to any portion of the sidewall of other portions of the MRI apparatus 2, and may include any appropriate number of windings depending upon imaging requirements. An exemplary draping 100 according to one embodiment may be positioned over the MRI apparatus 2 and will be described in more detail below. While one type of MRI apparatus 2 has been shown, it will be appreciated that the embodiments of the draping 100 are applicable to various other types of such apparatuses.

Figure 2:
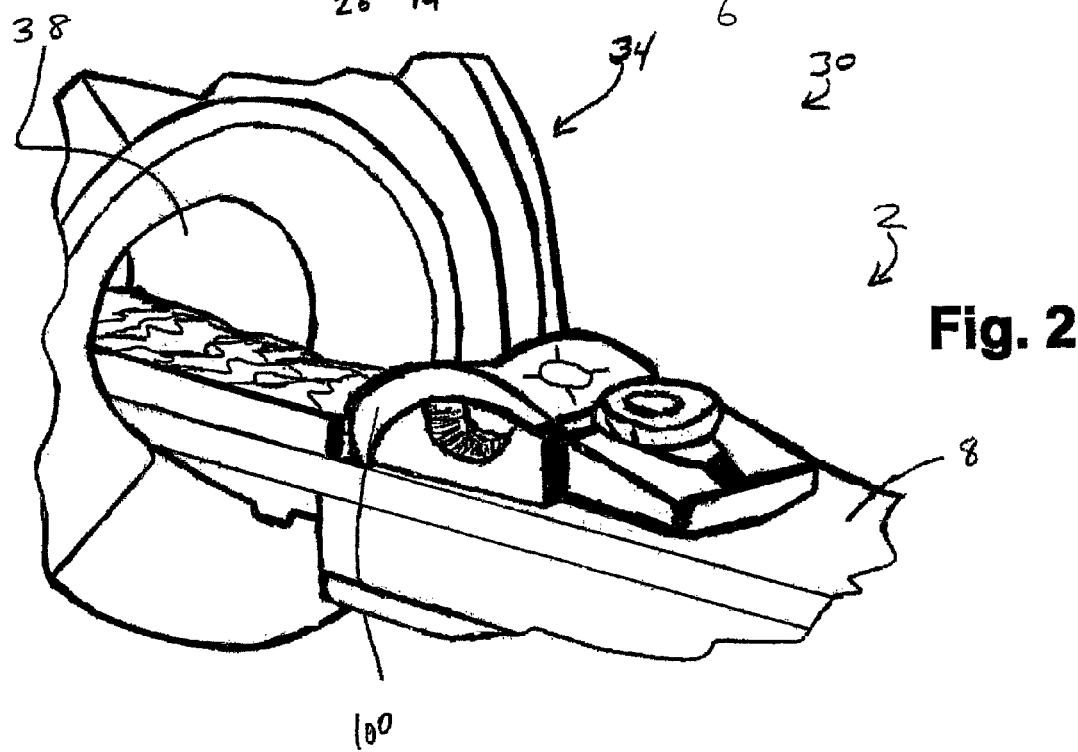
FIG. 2 illustrates a perspective view of an MRI system, and including the MRI apparatus and draping of FIG. 1.

An MRI system 30 is illustrated in FIG. 2, and may broadly include a housing 34 and the MRI apparatus 2 of FIG. 1. The housing 34 includes a primary magnet (not shown) and a central bore 38 that may accept or receive the MRI apparatus 2 for an MRI procedure of a patient. As such, the MRI apparatus 2 may be appropriately translatable or positionable into and/or out of the central bore 38 by way of sliding tracks, casters, and the like. After the primary magnet aligns the protons in the hydrogen atoms in a particular portion of a patient's body, the MRI apparatus 2 generates and directs RF signals to the body portion which momentarily knock the hydrogen atom protons out of alignment. Upon realignment after a RF signal pulse, the protons themselves emit RF signals which may be analyzed to detect specific body tissues. Operation of the MRI system 30 may be controlled from an operator console or other appropriate device (not shown).

Figure 3:
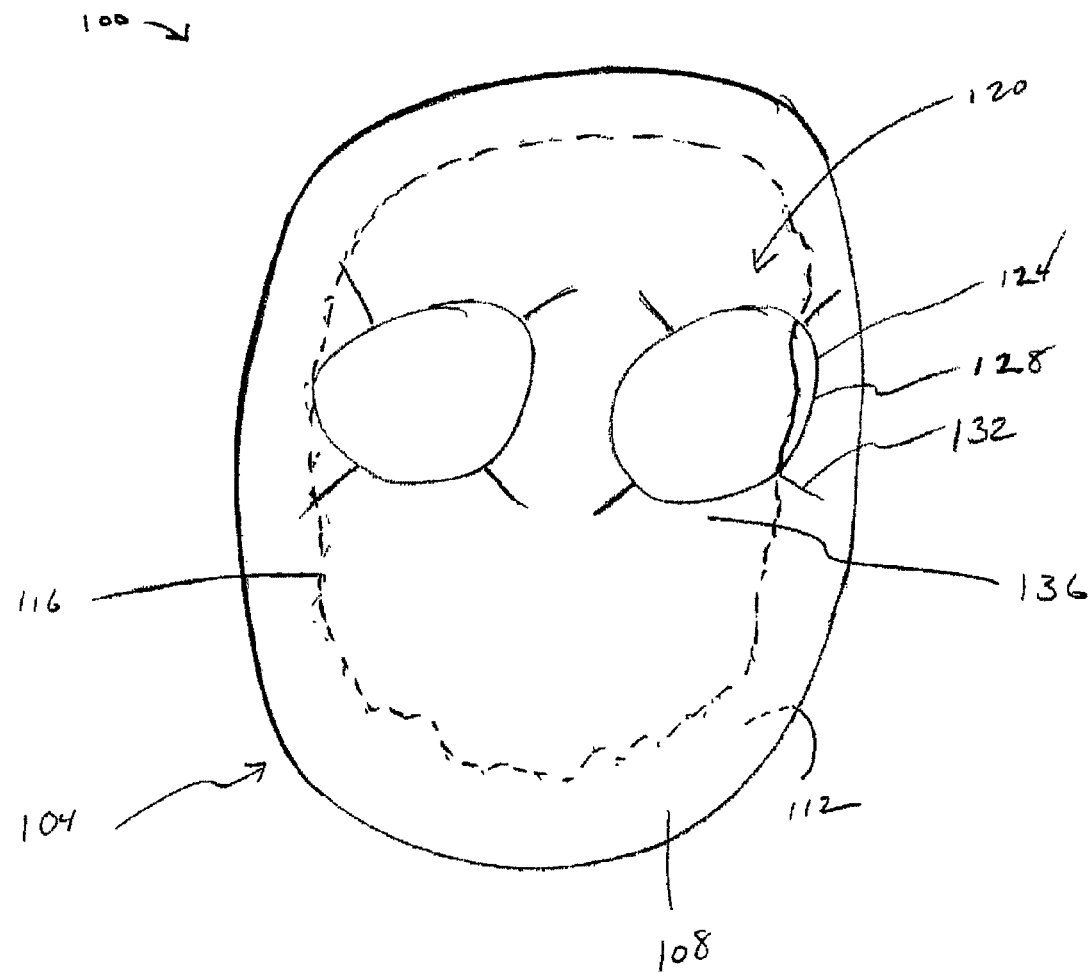
FIG. 3 illustrates a top view of a draping for an MRI apparatus.

FIG. 3 illustrates an exemplary draping 100 for an MRI apparatus including a breast coil, such as the MRI apparatus 2 illustrated in FIG. 1. The draping 100 may broadly include a barrier 104 having front and back surfaces 108, 112. The barrier 104 may be of shape that allows the barrier 104 to conform to the shape of an MRI apparatus; representative shapes include round, rectangular, and the like. Moreover, the barrier 104 serves to reduce or otherwise prevent contact between a patient and various portions of the MRI apparatus 2 that the patient's body might come into contact with, such as for instance the patient interface surface. As such, the barrier 104 may be constructed of at least one sterile flexible and/or pliable material and may be formed of any number of materials and/or layers such as of paper, cotton, and/or synthetic materials; the barrier may also be disposable (e.g. disposed of after a single MRI procedure or after use by an individual patient) or reusable (e.g. disposed of after multiple MRI procedures or used by an individual patient or used by multiple patients). In one embodiment, the barrier 104 may be constructed of a non-woven fabric. For instance, the barrier 104 may be constructed of a spunbond/meltblown/spunbond (SMS) non-woven fabric that may include polymers such as polypropylene and/or polyethylene. SMS materials may provide advantageous features such bacteria impermeability, fluid penetration resistance, softness and comfort, and the like. In other embodiments, the barrier 104 may also include a non-slip or non-skid surface or material to prevent or otherwise reduce undesired slipping or movement of the drape portion during a surgical/interventional procedure. Even further embodiments contemplate that the barrier 104 may contain fragrance or aromatherapy types of products such as oils or lotions to mask unpleasant odors in addition to improving the psychological and/or physical well-being of the patient.

The barrier 104 additionally includes a periphery 116 that may be appropriately secured around a portion of the MRI apparatus 2. The periphery 116 may define a border between the front and back surfaces 108, 112 and may conform to the overall shape of the barrier 104. At least one securing member (not shown) may be associated with the periphery 116 or other portion of the barrier 104. The securing member may provide a degree of adjustability for the barrier 104 and assist in securing the barrier 104 to a portion of the MRI apparatus 2 such as the housing 6 or patient interface surface. Moreover, the periphery 116 may be sized to encompass a periphery of the patient interface surface of each of a plurality of MRI apparatuses 2, at least some of the MRI apparatuses 2 having different sized housings 6, patient interface surfaces, and the like. In this regard, a single draping 100 may be used in conjunction with a number of MRI apparatuses regardless of the size, diameter, etc. of the housing 6 and patient interface surface of the MRI apparatuses 2. More specifically, the securing member may advantageously removably secure the draping 100 to the housing 6 or patient interface surface of each of a number of various sized MRI apparatuses 2.

The securing member may comprise any device that may secure the barrier 104 around a portion of the MRI apparatus. In some embodiments, the securing member may comprise at least one of elastic, hook and loop fasteners, string, tape, buttons, snaps, ribbons, ties, adhesives, tabs, hooking devices, sticky glue, belt interlocking devices, and other tightening and adjusting devices that allow the barrier to conform to the design of the MRI apparatus 2. However, other types of securing members are envisioned. In an exemplary embodiment, the elastic used in association with the draping 100 may allow the barrier 104 to be stretched for adjustment which results in complete coverage and alignment to the shape of the MRI apparatus 2.

The barrier 104 may also include features (not shown) that allow the barrier 104 to provide adjustable tension in all directions about an MRI apparatus 2. For instance, such features may include a cut out portion, slit, torn or notch in the barrier 104 to accommodate any fastening to another piece or portion of the equipment set-up. In one embodiment, such features are associated with the periphery 116; however, the features may be associated with other portions of the periphery 116. It should be appreciated that the barrier 104 may be adapted to cover other types of MRI apparatuses.

With continued reference to FIG. 3, the barrier 104 additionally includes at least one opening 120 for pendulantly receiving a portion of a patient, such as a breast. As will be described below, the barrier 104 may be positionable over the MRI apparatus 2 such that the opening 120 may be locatable over the aperture 14 in the MRI apparatus 2. As such, the barrier aligns and fits the shapes of the MRI apparatus 2. The patient and/or technologist may then position the breast through the opening 120 and into the MRI apparatus aperture 14 for an imaging procedure. While a pair of openings 120 is illustrated in FIG. 2, only one will be described. In other embodiments, the barrier may include more or less than a pair of openings 120.

The opening 120 is subject to a number of characterizations. One is that the opening 120 may be partially defined by at least one hole 124 having a periphery 128. The hole 124 may be sized to pendulantly accept a patient's breast, and as such, may be of a generally circular shape so as to conform to a cross-section of a patient's breast taken along a plane that is generally parallel to the patient's chest. As will be later described, the diameter of the hole 124 may be less than the diameter of the base of a typical breast. In one embodiment, the hole may be about 4 inches in diameter, and more preferably about 3¼ inches in diameter. However, in other embodiments the hole 124 may be of other shapes such as oval, rectangular, and the like, and may have diameters greater than or less than the diameter of the base of a patient's breast.

The shape of the hole 124 may at least closely match the shape of an MRI apparatus aperture 14. In this regard, the hole 124 and the aperture 14 may have equivalent or substantially equivalent diameters if circular or lengths and widths if rectangular, for instance. In other embodiments, the diameter of the hole 124 of the opening 120 may of a size that allows the periphery 128 of the hole 124 of the opening 120 to be encompassed by the periphery 18 of the aperture 14 of a number of MRI apparatuses, at least some of the MRI apparatuses having apertures of different sizes or shapes. As such, a single draping 100 may advantageously be used in conjunction with a number of MRI apparatuses regardless of the size or shape of the aperture 14 of the MRI apparatuses. More specifically, the opening 120 or hole 124 may be sized such that the opening 120 or hole 124 is at least substantially aligned over or encompassed by the aperture 14 of any number of various sized MRI apparatuses and thus primed for entry of a patient's breast when the barrier is positioned over the patient interface surface. The hole 124 may be cut out of the barrier 104 after production of the barrier 104 or may be formed as part of the production process of the barrier 104.

Another characterization of the opening 120 is that it may be partially defined by at least one notch 132 that may be in the form of slits, slots, cuts, and the like. The notch 132 generally intersects the hole 124, and then extends in a direction away from the hole 124 for a distance. In one embodiment, the notch 132 extends away from the hole 124 for a distance of about 2½ inches, more preferably for about 2 inches and even more preferably for about 1 inch. The notch 132 may increase the area of the opening 120 during introduction of a breast into the opening 120. In this regard, the notch 132 may increase patient comfort in addition to providing a degree of adjustability to the opening 120 to accommodate breasts and MRI apparatus apertures 14 of various sizes. As illustrated in FIG. 2, the opening 120 may be partially defined by at least four notches 132 spaced around the periphery 128 of the hole 124. While the notches 132 are shown as being substantially equally spaced from each other, other configurations and orientations of notches are within the scope of the embodiment. Also, more or less than four notches 132 can be utilized with barrier 104.

At least one flap 136 may be partially disposed between and partially defined by two adjacent notches 132. The flap 136 may be locatable between at least a portion of the MRI apparatus 2 and a portion of the patient's breast to protect the patient from germs and infection diseases (e.g. MRSA) in addition to providing the patient with warmth and comfort. For instance, each flap 136 may be locatable between a patient's breast and a sidewall 22 and/or coil of the MRI apparatus 2. As shown, the draping 100 may include four flaps 136, each of the flaps 136 being defined by at least two notches 132.

In use, the barrier 104 may initially be positioned over and secured on the MRI apparatus 2 such that the opening 120 may be positionable over an MRI apparatus aperture 14. Thereafter, introduction or positioning of a patient's breast through the opening 120 may cause each flap 136 to move in a direction towards and into the MRI apparatus aperture 14 or generally in a direction from the front surface 108 towards the back surface 112 of the barrier 104 until each flap 136 is positioned between a portion of the MRI apparatus 2 and a portion of the patient's breast. Once so positioned, the patient's breast may be generally inhibited from direct contact with a portion of the MRI apparatus 2 because of the presence of each flap 136 between the portion of the MRI apparatus 2 and the breast. Additional flaps may be created in the barrier 104 to create a desired degree of comfort, protection and the like.

Although the flaps 136 have been described as being disposed into the MRI apparatus aperture 14 by the introduction or positioning of the breast into the opening 124 and aperture 14, other methods of positioning each flap 136 between a portion of the breast and a portion of the MRI apparatus 2 are contemplated. For instance and as will be described below, the flaps may be pre-positioned or otherwise appropriately disposed downward or in a direction away from the opening 124 by hospital technicians and the like before the breast is positioned through the opening 124 and aperture 14. In such embodiments, introduction of the patient's breast may only minimally urge the flaps toward the MRI machine breast coil aperture or may not urge such flaps toward the aperture at all.

Figure 4:
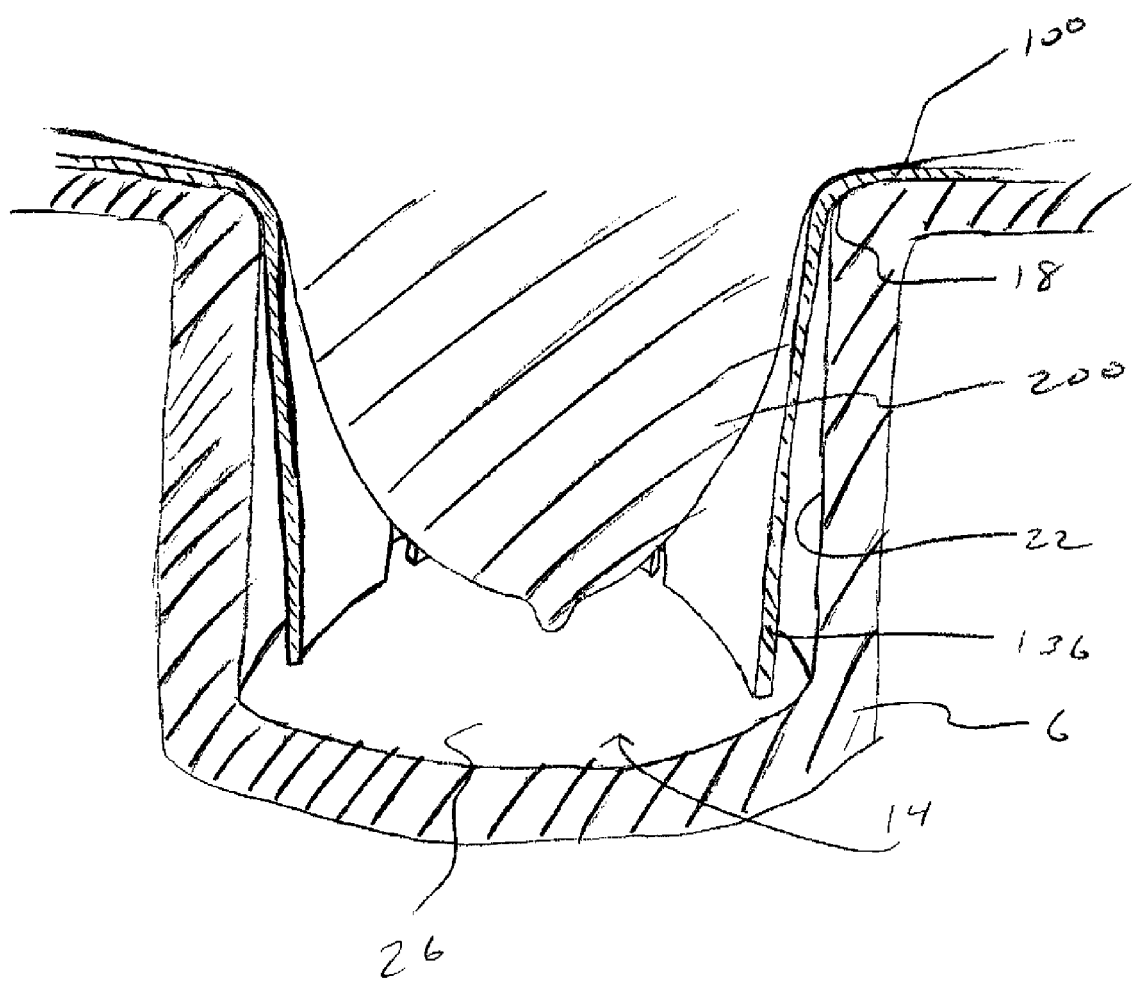
FIG. 4 illustrates a cross-sectional view through the line 4-4 of FIG. 1 and including a draping disposed over the MRI apparatus and a patient breast disposed within the aperture of the MRI apparatus.

FIG. 4 is a cross-sectional view along the line 4-4 of FIG. 1, but additionally with a draping 100 appropriately positioned over the MRI apparatus 2 and a breast 200 located within the aperture 14. As may be seen, the draping 100 may provide patient relief for pressure points created between the periphery 18 of the aperture 14 and the breast 200 of the patient. Moreover, because each flap 136 may be generally located between a portion of the MRI apparatus 2 (e.g. sidewall 22 and/or coil) and the patient breast 200, disease and other contaminants are prevented or at least inhibited from proceeding between the MRI apparatus 2 and the patient breast 200. Each flap 136 may be of a length that such that it extends substantially to a base 26 of the aperture 14 as is illustrated in FIG. 4. In other embodiments, each of one or more of the flaps 136 may be of a shorter length such that it extends just past periphery 18, or even to lengths between just past the periphery 18 and the length as shown in FIG. 4. In even further embodiments, each of one or more of the flaps 136 may be of a length such that it rests on and covers a portion of the base 26 of the aperture 14. As such, any direct contact between the patient breast 200 and such base 26 may be avoided or at least reduced. Moreover, wicking or other appropriate material may be incorporated with or even comprise one or more of the flaps 136 that may be operable to wick or otherwise draw blood and/or other fluids out of the aperture 14 during a biopsy or other procedure. Numerous other benefits and advantages will be recognized and appreciated with reference to the various embodiments.

Figure 5:
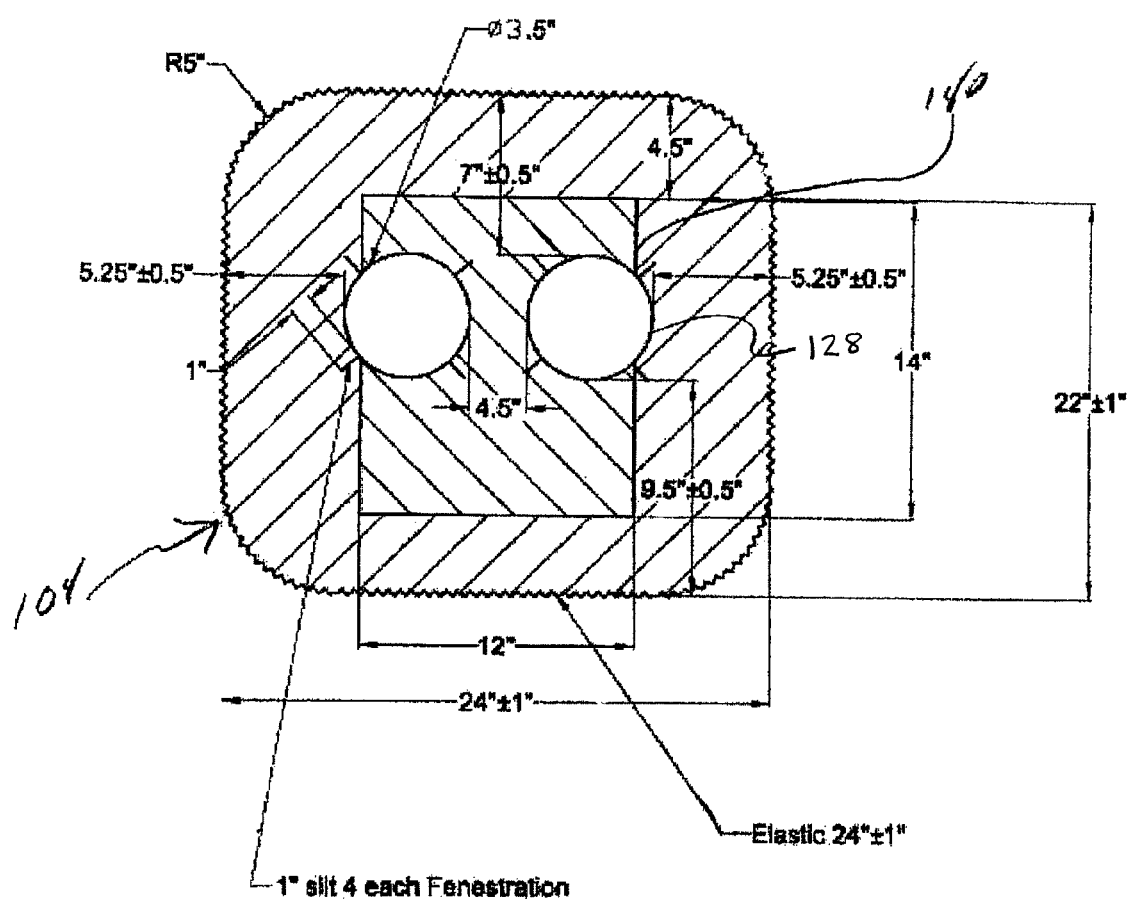
FIG. 5 illustrates a bottom view of the draping of FIG. 3.
Figure 6:
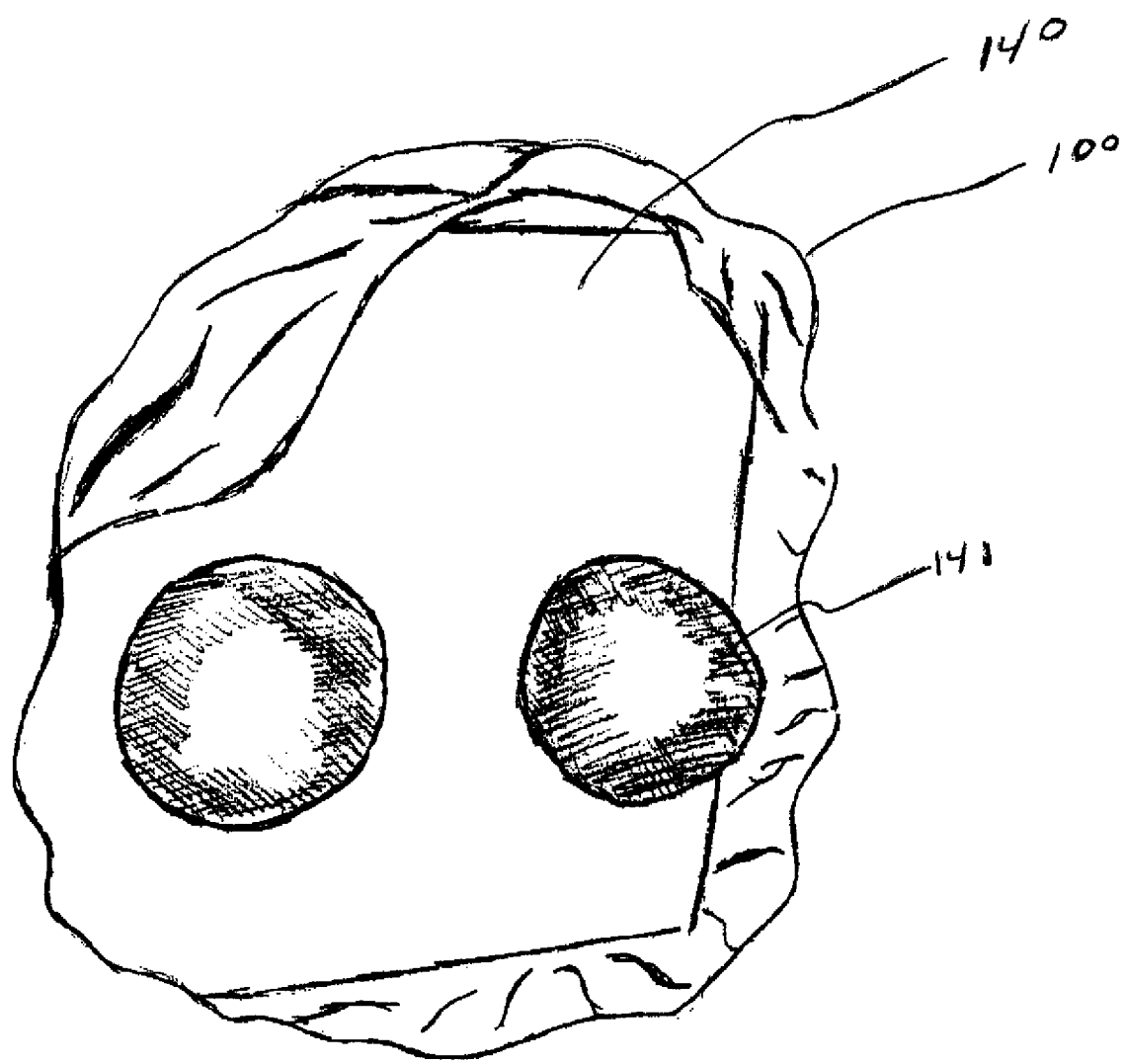
FIG. 6 illustrates another bottom view of the draping of FIG. 3.

FIGS. 5-6 illustrate bottom views of the draping 100 of FIG. 3. The barrier 104 may comprise at least one padding member 140 that may be in the form of an absorbing member and/or cushion. The padding member 140 may serve to absorb or receive liquids and other debris that may be situated or associated with the MRI apparatus 2 and/or the patient. Moreover, the padding member 140 may increase patient comfort and warmth during an MRI procedure in addition to further increasing the protective aspect of the barrier 104. For instance, smaller sized breasts often cannot be positioned far enough into the breast coil (represented schematically by reference numeral 141 in FIG. 6) for imaging due in part to the thickness of the MRI apparatus manufacturer's padding or sleeves around and/or adjacent the breast coil and a patient interface surface. Because the manufacturer's padding may be removed for such procedures, patients may experience an increase in chafing, irritation, and the like, and an overall decrease in comfort. Additionally, the MRI apparatus 2 often includes tabs or other protruding devices used to attach the manufacturer's padding to the MRI apparatus 2. The padding member 140 may provide increased comfort and protection for patients in such situations.

As shown, the padding member 140 may be generally disposed about a portion of each of the openings 120 because such areas of the barrier 104 may experience a larger load from the patient's body resting on the patient interface surface during the MRI procedure. Further, the padding member 140 may serve to absorb liquids disposed within or near the apertures or other portions of the MRI apparatus 2. In some embodiments, the padding member 140 may be located over an entirety of the back surface 112 of the barrier 104. In other embodiments, the padding member 140 may be associated with at least a portion of the front surface 108 either individually or along with at least a portion of the back surface 112. The padding member 140 may also not even be associated with the barrier 104 if the barrier 104 material already provides sufficient comfort, protection and warmth for the patient.

The padding member 140 may be in the form of at least one of a layer of felt, gelatinous materials, cottons, fabric and the like. Moreover, the padding member 140 may include a single type of material, or may include different combinations of materials to provide a desired degree of comfort, protection, and warmth for example. In one embodiment, the padding member 140 may be constructed of a pulp based material such as Airlaid®. Airlaid® is a soft, non-woven, highly absorbent and low leakage cellulose-based fabric that may have a web of pulp fibers that may be bonded by any appropriate technique (e.g. latex bonding, thermal bonding, and/or hydrogen bonding). It may absorb more moisture than common cellulose while remaining more tear-proof and dimensionally stable. In other embodiments, the Airlaid® may be bonded or otherwise disposed over a layer of polyethylene. Moreover, the padding member 140 may be appropriately secured to the back surface 112 of the barrier 104 or other portions of the barrier such as the front surface 108. For instance, the padding member 140 may be secured to the barrier 104 by adhesives, stitching, etc.

Figure 7:
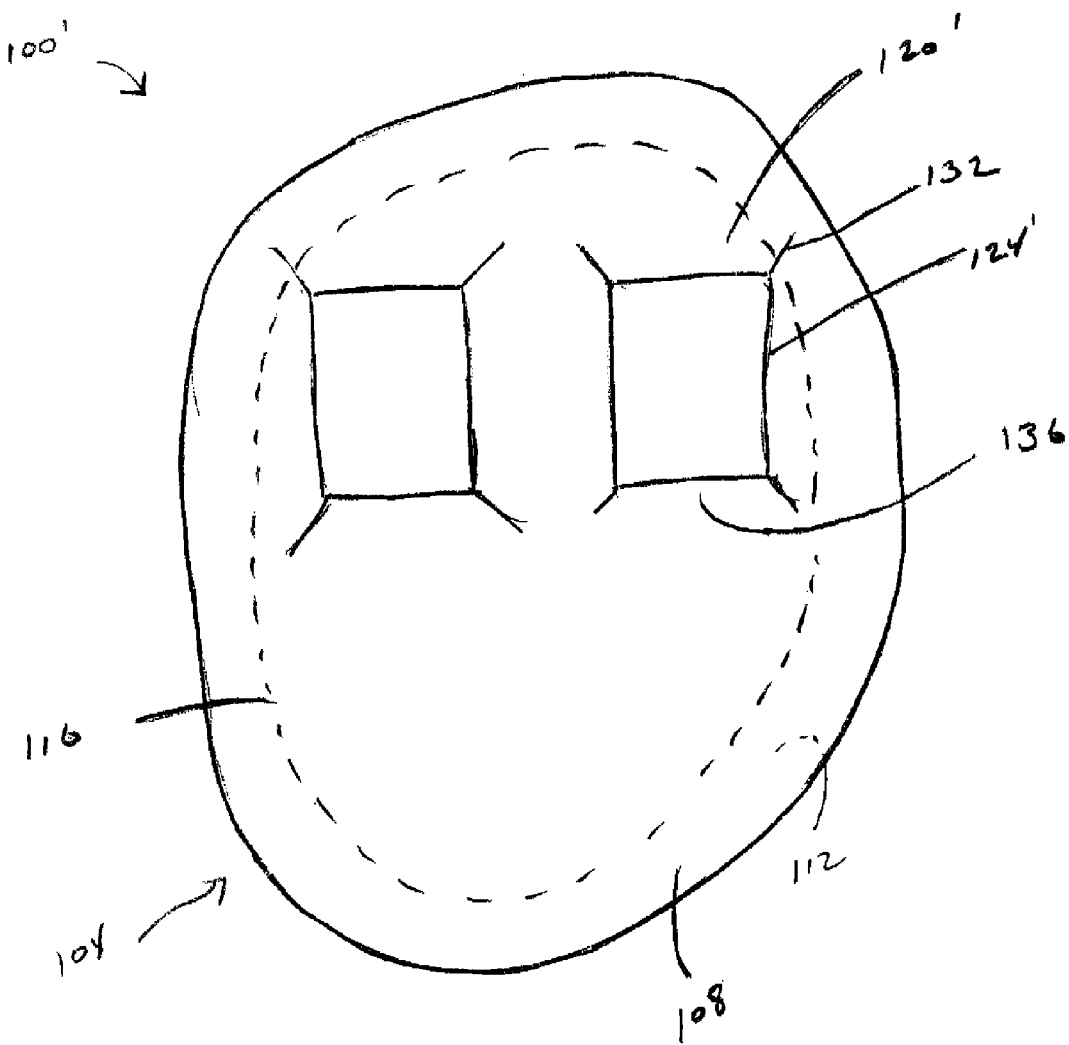
FIG. 7 illustrates a top view of another draping for an MRI apparatus.
Figure 8:
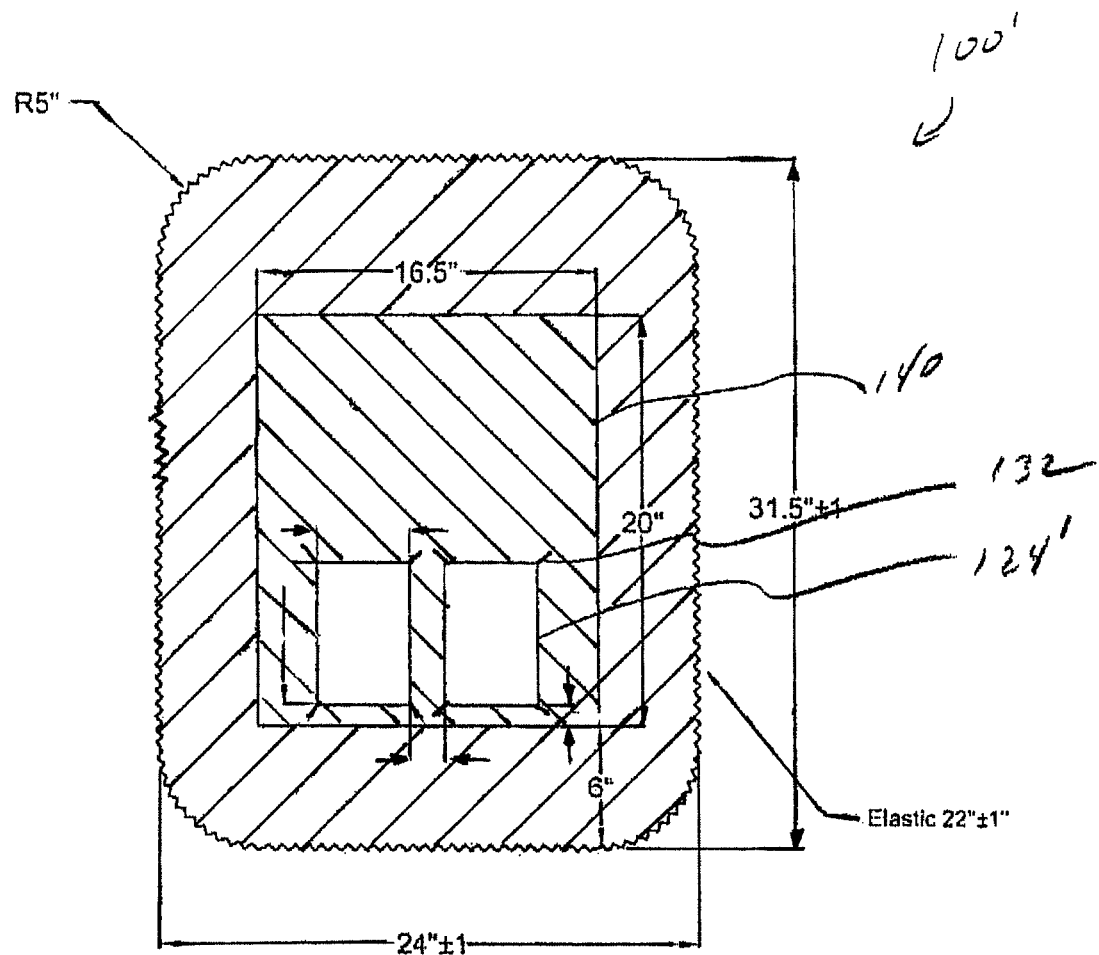
FIG. 8 illustrates a bottom view of the draping of FIG. 7.

FIGS. 7 and 8 present a variation of the draping 100 of FIGS. 3-6. Corresponding components between the two embodiments are identified by a common reference numeral. Those corresponding components that differ in at least some respect are identified by a "single prime" designation in FIGS. 7 and 8. The primary difference between the draping 100 of FIGS. 3-6 and the draping 100' of FIGS. 7 and 8 is that the draping 100' of FIGS. 7 and 8 includes openings 120' with at least one rectangularly-shaped hole 124'. The rectangularly-shaped hole 124' of the opening 120' of the draping 100' may be used with an MRI apparatus aperture of a similar shape. Matching the shape of the rectangularly-shaped hole 124' of the draping 100' to an MRI apparatus aperture facilitates alignment of the opening 120' over the MRI apparatus aperture when the draping 100' is disposed over the MRI apparatus. However, as previously discussed, the hole 124' of the opening 120' may be sized to be encompassed or enveloped by the aperture 14 of the MRI apparatus 2 so that the draping 100' can be used in conjunction with a plurality of MRI apparatuses 2 of various sizes. Further, use of the draping 100' with at least one rectangularly-shaped hole 124' may provide additional levels of adjustability to accommodate breasts of various sizes.

Figure 9:
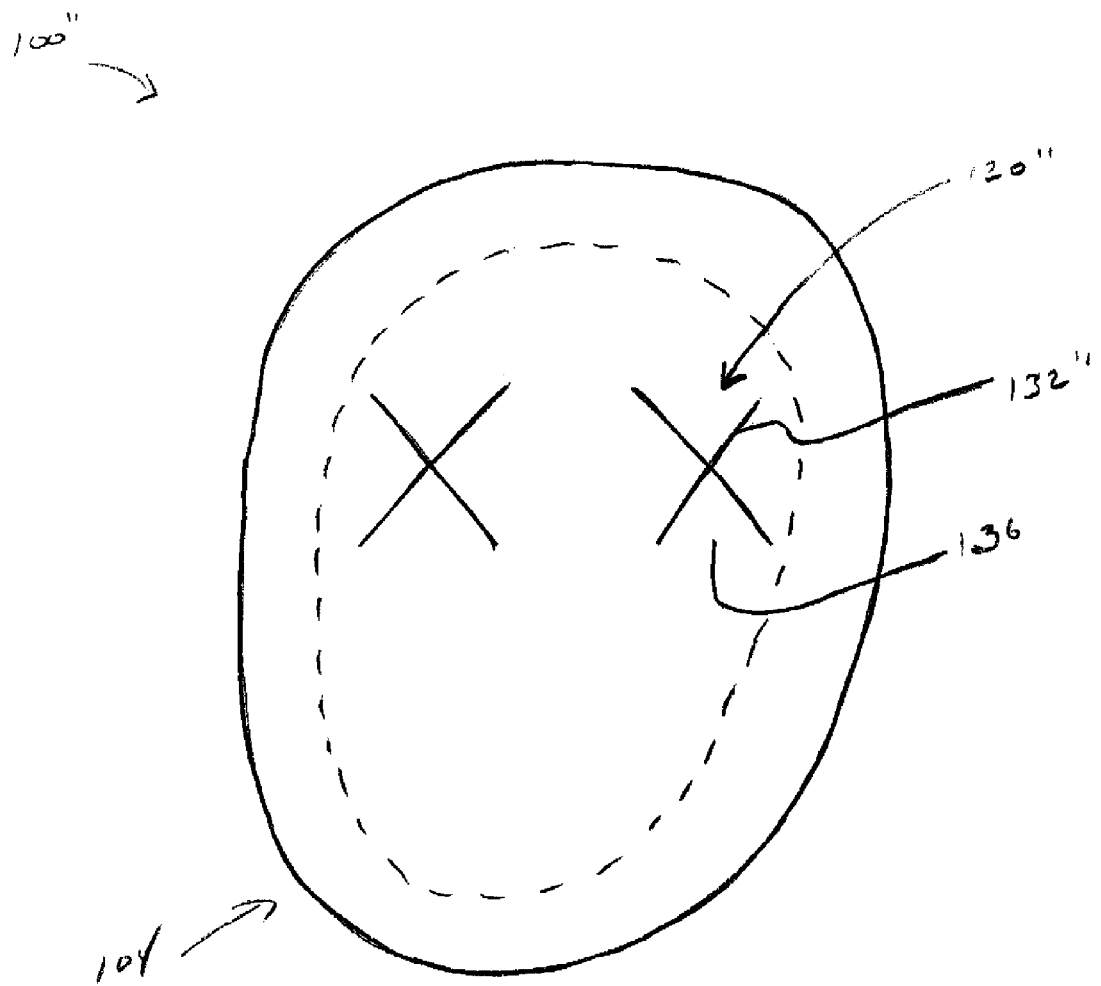
FIG. 9 illustrates a top view of another draping for an MRI apparatus.

FIG. 9 presents yet another variation of the draping 100 of FIGS. 3-6. Corresponding components between the two embodiments are identified by a common reference numeral. Those corresponding components that differ in at least some respect are identified by a "double prime" designation in FIG. 9. In this embodiment, the draping 100" may include an opening 120" that may be partially defined by a plurality of notches 132', each of the notches 132" intersecting at least one of the other notches 132". As illustrated in FIG. 9, the opening 120" may include a pair of intersecting notches 132" in the form of an "X" shape. The notches 132" may partially define the flaps 136, the flaps 136 being operable to be positioned between a patient's breast and a portion of the MRI apparatus to provide warmth and comfort and to prevent or otherwise reduce the transmission of germs and other infections between a patient and a portion of the MRI apparatus or other equipment.

In other embodiments, the opening 120" may include fewer or more than a pair of notches 132" with varying degrees of intersection. For instance, the opening 120" may include a primary notch 132" with a plurality of secondary notches 132" emanating from either side of the primary notch 132" and partially defining or forming the flaps 136. Moreover, the notches 132" may be of varying lengths and widths. The opening 120" reduces manufacturing steps because of the absence of a hole as in other embodiments. Additionally, the absence of a hole in the opening 120" may provide a tighter or more snug and comfortable feel for a patient during an MRI procedure. Other embodiments of the openings 120" are also contemplated.

Figure 10:
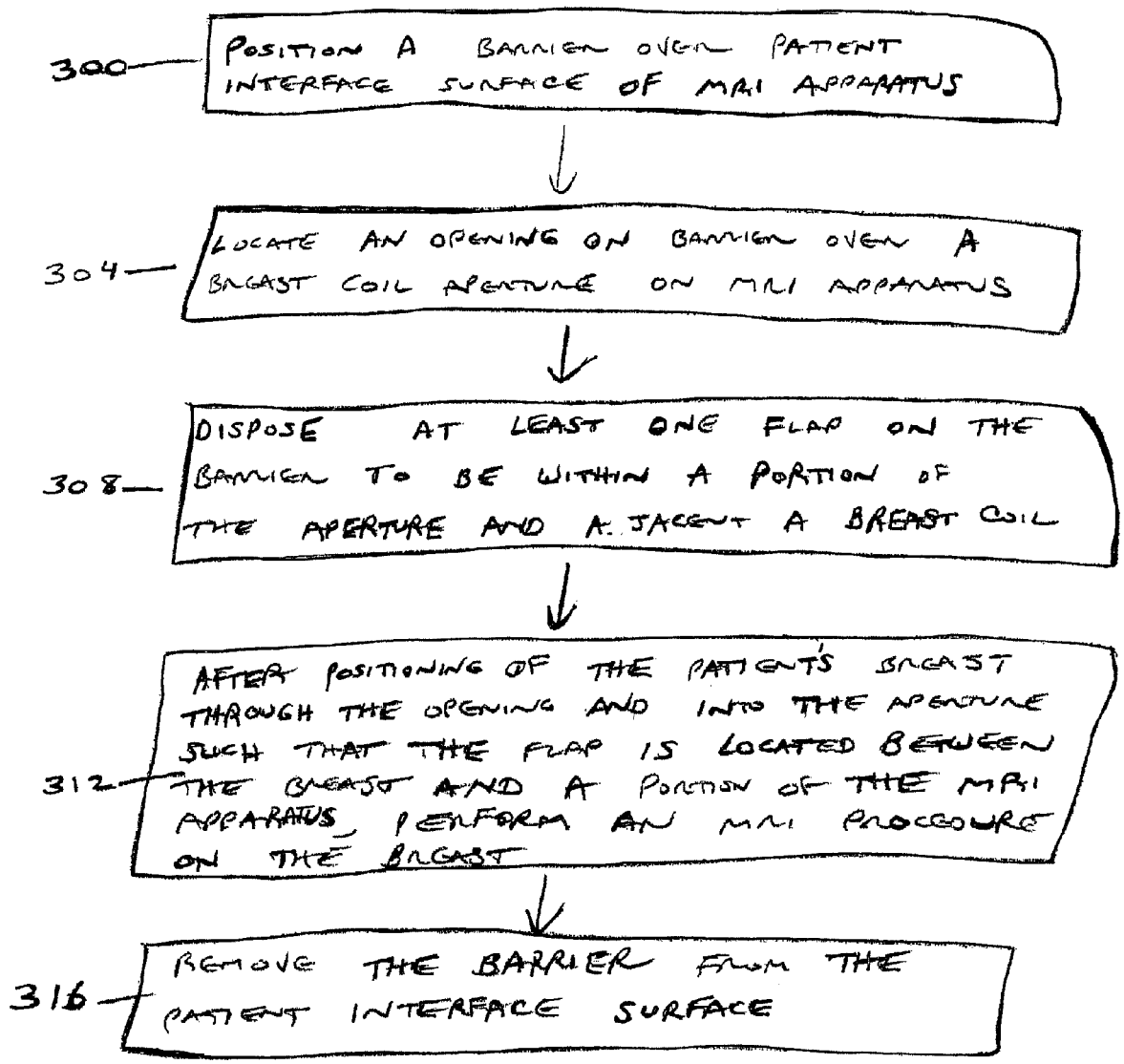
FIG. 10 is a flowchart illustrating a method of positioning a barrier over a patient interface surface of an MRI apparatus.

FIG. 10 is a flowchart illustrating one method of use of any of the embodiments of the draping. It will be appreciated that other methods of the use of the draping of the embodiments are contemplated. In an exemplary embodiment, FIG. 10 depicts a method for reducing contact between a patient breast and a portion of a Magnetic Resonance Imaging (MRI) apparatus, the MRI apparatus including a patient interface surface, an aperture extending through the patient interface surface, and a coil associated with the aperture.

Initially in step 300, a barrier may be positioned over the patient interface surface (i.e. patient interface surface of the MRI apparatus 2 of FIG. 1). Either the front or back surface of the barrier may be placed in direct contact with the patient interface surface. The barrier may conform to an overall shape or configuration of the MRI apparatus and as such may be generally circular, rectangular, and the like. Such shapes facilitate the positioning or aligning of the barrier over the MRI apparatus. However, if the barrier is also secured to the MRI apparatus as will be described below, the shape of the barrier need not necessarily conform to the overall shape of the MRI apparatus.

In some embodiments, the barrier can additionally include a periphery that may be appropriately secured around a portion of the MRI apparatus. At least one securing member may be associated with the periphery or other portion of the barrier. The securing member may provide a degree of adjustability for the barrier and assist in securing the barrier to the patient interface surface. Moreover, the periphery may be sized to encompass a periphery of the patient interface surface of each of a plurality of MRI apparatuses, at least some of the MRI apparatuses having different sized patient interface surfaces. Thus, a single draping or barrier may be used in conjunction with a number of MRI apparatuses regardless of the size, diameter, etc. of the patient interface surface of the MRI apparatuses. More specifically, the securing member may advantageously removably secure the draping or barrier to the patient interface surface of each of a number of various sized MRI apparatuses.

Thereafter in step 304, at least one barrier opening may be appropriately located over a breast coil aperture of the MRI apparatus. As previously discussed, the barrier opening allows access to the breast coil aperture for a patient's breast for a subsequent MRI procedure. While the location of at least one barrier opening has been described, additional barrier openings may be located over additional MRI apparatus apertures for the imaging of additional breasts. In some embodiments, step 304 may include aligning the barrier opening and the aperture of the MRI apparatus which further facilitates introduction of a breast into the MRI apparatus aperture. Aligning the barrier opening and the MRI apparatus aperture may include aligning the perimeters of the barrier opening and the MRI apparatus aperture if both are of a substantially similar size and/or diameter. In other variations, such aligning may comprise arranging a center axis of each of the barrier opening and the aperture of the MRI apparatus to be collinear with each other. In even further variations, the aligning may comprise arranging a periphery of the opening such that it is encompassed or enveloped by the aperture of a number of MRI apparatuses, at least some of which have various sized apertures. In this regard, the draping or barrier can be designed such that the opening is primed for the introduction of a patient breast through the opening and aperture as soon as the barrier is positioned over the patient interface surface. Once the barrier has been positioned over the patient interface surface and a barrier opening has been located over an MRI machine aperture, at least one flap adjacent to the barrier opening may be disposed to be within a portion of the MRI apparatus aperture and adjacent a coil in step 308. As discussed previously, positioning the flap to be in such a location serves to reduce or prevent cross-contamination of germs and diseases for instance between a portion of a patient (e.g. breast) and a portion of the MRI apparatus (e.g. sidewall of aperture and/or coil). Additional flaps may be so disposed for increased comfort and decreased cross-contamination, and such flaps may be equidistantly spaced around a center axis of the barrier opening. Moreover, such disposition of the flap may be subject to a number of characterizations. One is that disposing the flap to be within the MRI apparatus aperture may include advancing at least a portion of at least one flap into a portion of the MRI apparatus aperture. As such, at least a portion of the flap may generally extend away from the barrier opening.

In one variation, advancing of the flap into the MRI apparatus aperture may be accomplished by locating a patient breast through the barrier opening and aperture of the MRI apparatus. More specifically, upon introduction of the breast through the barrier opening, the breast may make contact with the flap and generally urge the flap away from the barrier opening such that the flap may be interposed between at least a portion of the aperture sidewall and/or coil and at least a portion of the patient breast. The patient may either position the breast through the opening or else may be directed to do so by for instance a hospital employee (e.g. technician, doctor). Although introduction of the patient breast has been described after the barrier opening has been located over the MRI apparatus aperture, the patient breast may also be introduced into the barrier opening before the barrier opening is located over the MRI apparatus aperture, or even before the barrier has been positioned over the patient interface surface of the MRI apparatus. In such situations, after the breast has been introduced into the barrier opening, the patient may then appropriately position the breast into the MRI apparatus aperture such that the flap may be located between the breast and a portion of the MRI apparatus.

In another variation, advancing of the flap comprises pushing the flap into the portion of the aperture of the MRI apparatus. For instance, hospital technicians and the like or even the patient may urge or push the flap into the MRI apparatus aperture such that the flap is generally adjacent the coil. Pushing or urging of the flap may position, flex, fold, crease and/or bend the flap. In some embodiments, the flap may generally stay or remain within the MRI apparatus aperture after the pushing or urging of the flap. For instance, hook and loop fasteners may be used on portions of the flap and a portion of the MRI apparatus to detachably secure the flap to the MRI apparatus. After an imaging procedure, the flap may be easily removed or disengaged from the MRI apparatus. In other embodiments, a hospital technician or patient may need to maintain continuous contacts on the flap until after the breast has been introduced through the barrier opening and into the MRI apparatus aperture.

Another characterization of disposing of at least one flap to be within a portion of the MRI apparatus aperture and adjacent a coil may include maneuvering the flap at least partially away from the barrier opening, and then arranging the flap to be within a portion of the MRI apparatus aperture. For instance, the flap may be "pre-folded" or otherwise configured to protrude or extend away from the barrier opening before the flap has been introduced into the MRI apparatus aperture. As such, a hospital employee or the patient may articulate or push the flap (e.g. by positioning, folding, creasing, bending and/or flexing the flap), and then move the flap into the MRI apparatus aperture. For instance, arranging the flap to be within the MRI apparatus aperture may include placing the flap into the portion of the aperture of the MRI apparatus and adjacent the coil, and the placing may include pushing, inserting, and the like. Maneuvering or otherwise appropriately articulating the flap before introduction into the MRI apparatus aperture may facilitate subsequent introduction of the breast into the MRI apparatus aperture.

In step 312, after the patient's breast has been positioned through the barrier opening and into the aperture such that at least one flap is located between the breast and a portion of the MRI apparatus (e.g. sidewall), the hospital technician or doctor performs an MRI procedure on the pendulant breast. Because the barrier has been positioned over the patient interface surface of the MRI apparatus, direct patient contact with the patient interface surface is inhibited, cross-contamination between the patient and the MRI apparatus may be prevented or at least reduced, and patient comfort may be increased. Further, the flap additionally serves to prevent or reduce direct contact between portions of the MRI apparatus aperture; as such, cross-contamination may be reduced and patient comfort may be increased. Moreover, the barrier and corresponding flap(s) are constructed of a material that does not inhibit the MRI procedure. In step 316, the barrier may be removed from the patient interface surface and discarded after the imaging procedure. In this regard, the barrier may be disposable or alternatively reusable.

At any point in the method, the barrier may be appropriately secured to a portion of the MRI apparatus. For instance, at least one securing member interconnected to the barrier may be manipulated so as to detachably connect the barrier to the patient interface surface and restrict relative movement between the barrier and the MRI apparatus. Such securing member may additionally serve to constrain portions of the barrier that may interfere with an imaging procedure and comprise elastics, hook and loop, string, tape, snaps, ribbons, sticky glue, buttons, ties and/or tab hooks. However, other types of appropriate securing members may be utilized with the barrier to restrain movement between the barrier and the MRI apparatus.

As previously described, MRI apparatuses are often provided with padding or cushioning that may be supplied by the apparatus manufacturer. The padding or cushioning may be positioned adjacent the MRI apparatus apertures because such locations often cause increased patient discomfort due to the creation of pressure points adjacent patient breasts. While meant to enhance patient comfort, such padding or cushioning may interfere with the imaging of small-breasted patients because such breasts cannot hang or be appropriately introduced far enough into the MRI apparatus aperture to allow for an effective imaging procedure. In this regard, the method may additionally comprise (preferably before the positioning step) removing at least one member associated with a portion of the patient interface surface to allow for effective imaging of small-breasted patients. The removed member may include a layer of flexible material such as the padding and/or cushioning members. In other embodiments, the removed member may comprise any other member associated with the MRI apparatus that may interfere with an MRI procedure.

The above-noted embodiments are for the purpose of illustration and are not intended to limit the scope of the present invention or patent. Rather, various modifications, adaptations and extensions of the invention will be apparent to those skilled in the art and are intended to be within the scope of the present invention as contemplated by the claims that follow.

What is claimed is:

1. A method for reducing contact between a patient and a portion of a Magnetic Resonance Imaging (MRI) apparatus, the MRI apparatus including a patient interface surface and an aperture extending through the patient interface surface, the method comprising:

positioning a barrier over at least a portion of the patient interface surface, the barrier comprising an opening;

arranging a periphery of the barrier to encompass a periphery of the patient interface surface;

securing the barrier to the MRI apparatus;

locating the opening over the aperture of the MRI apparatus;

inserting a patient breast through the barrier opening and into the aperture of the MRI apparatus; and manipulating a plurality of flaps of the barrier surrounding the opening to be within the aperture of the MRI apparatus and adjacent a sidewall and/or coil of the MRI apparatus, wherein the plurality of flaps are interposed between a) the patient breast, and b) the sidewall and/or coil of the MRI apparatus, and wherein at least a portion of the manipulating step occurs via the inserting step.

2. The method of claim 1, wherein the locating step further comprises arranging a periphery of the opening to be encompassed by a periphery of the aperture.

3. The method of claim 1, wherein the locating step further comprises:
aligning the barrier opening and the aperture of the MRI apparatus.

4. The method of claim 3, wherein the aligning step further comprises arranging a center axis of each of the opening and the aperture of the MRI apparatus to be collinear with each other.

5. The method of claim 1, wherein the securing step further comprises securing the barrier to the patient interface surface.

6. The method of claim 5, wherein the securing step further comprises securing the barrier to a ledge associated with the patient interface surface.

7. The method of claim 1, wherein the securing step further comprises:
manipulating at least one securing member interconnected to the barrier to detachably connect the barrier to the periphery of the MRI apparatus to restrict relative movement between the barrier and the MRI apparatus.

8. The method of claim 7, wherein the at least one securing member is comprises at least one of: elastic, hook and loop, string, tape, snaps, ribbons, sticky glue, buttons, ties and tab hooks.

9. A method for reducing contact between a patient and a portion of a Magnetic Resonance Imaging (MRI) apparatus, wherein the MRI apparatus includes a patient interface surface and an aperture extending through the patient interface surface, wherein the aperture is at least partially surrounded by a sidewall and/or coil of the MRI apparatus, and wherein the method comprises:
positioning a barrier over at least a portion of the patient interface surface, the barrier comprising an opening inside a periphery thereof, wherein the positioning step comprises arranging a periphery of the barrier to encompass a periphery of the MRI apparatus;
locating the opening over the aperture of the MRI apparatus;
positioning a patient breast into the opening of the barrier and the aperture of the MRI apparatus;
manipulating, during the positioning step, a flap of the barrier from a first position to a second position that is within the aperture of the MRI apparatus and adjacent the sidewall and/or coil, wherein the flap is configured to separate the patient from the sidewall and/or coil.

10. The method of claim 9, wherein the manipulating step further comprises manipulating a plurality of flaps of the barrier from first positions to second positions that are within a portion of the aperture of the MRI apparatus and adjacent the sidewall and/or coil.

11. The method of claim 9, further comprising:
securing the barrier to the MRI apparatus.

12. The method of claim 11, wherein the securing step comprises securing the barrier to the MRI apparatus using elastic.

13. The method of claim 9, wherein the positioning step further comprises positioning the barrier over at least a portion of the patient interface surface without regard to the size of the patient interface surface.

14. The method of claim 9, wherein the locating step further comprises locating the opening over the aperture of the MRI apparatus without regard to the size of the aperture.

15. The method of claim 9, wherein the locating step comprises arranging a periphery of the opening to be encompassed by a periphery of the aperture.

16. The method of claim 9, wherein the locating step comprises aligning the opening and the aperture.

17. The method of claim 9, wherein the first position of the flap is substantially parallel to the patient interface surface, and wherein the second position of the flap is other than parallel to the patient interface surface.

18. The method of claim 17, wherein the second position of the flap is substantially perpendicular to the patient interface surface.

19. The method of claim 9, wherein the flap forms a portion of a periphery of the at least one opening.

* * * * *